US012559439B2

(12) United States Patent
Kuchimanchi et al.

(10) Patent No.: US 12,559,439 B2
(45) Date of Patent: Feb. 24, 2026

(54) NATURAL ORGANIC NANO-FERTILIZERS AND THEIR PROCESS OF PRODUCTION

(71) Applicants: Venkata Satya Sarveswara Sairam Kuchimanchi, Secunderabad (IN); Vaishnavi Kuchimanchi, Secunderabad (IN)

(72) Inventors: Venkata Satya Sarveswara Sairam Kuchimanchi, Secunderabad (IN); Vaishnavi Kuchimanchi, Secunderabad (IN)

( * ) Notice: Subject to any disclaimer, the term of this patent is extended or adjusted under 35 U.S.C. 154(b) by 855 days.

(21) Appl. No.: 17/779,325

(22) PCT Filed: Jul. 8, 2020

(86) PCT No.: PCT/IN2020/050596
§ 371 (c)(1),
(2) Date: May 24, 2022

(87) PCT Pub. No.: WO2021/234718
PCT Pub. Date: Nov. 25, 2021

(65) Prior Publication Data
US 2023/0002291 A1     Jan. 5, 2023

(30) Foreign Application Priority Data
May 21, 2020    (IN) ............................. 202041021354

(51) Int. Cl.
| | |
|---|---|
| *C05F 17/20* | (2020.01) |
| *C05F 11/00* | (2006.01) |
| *C05F 17/40* | (2020.01) |
| *C05G 5/10* | (2020.01) |
| *C12N 1/145* | (2026.01) |
| *C12N 1/205* | (2026.01) |
| *C12R 1/225* | (2006.01) |
| *C12R 1/66* | (2006.01) |
| *C12R 1/685* | (2006.01) |

(52) U.S. Cl.
CPC .............. *C05F 17/20* (2020.01); *C05F 11/00* (2013.01); *C05F 17/40* (2020.01); *C05G 5/10* (2020.02); *C12N 1/145* (2021.05); *C12N 1/205* (2021.05); *C12R 2001/225* (2021.05); *C12R 2001/66* (2021.05); *C12R 2001/685* (2021.05)

(58) Field of Classification Search
CPC ...... C05F 17/20; C05G 5/10; C12R 2001/225
See application file for complete search history.

(56) References Cited

FOREIGN PATENT DOCUMENTS

| | | |
|---|---|---|
| CN | 101113120 A | 1/2008 |
| CN | 106242712 A | 12/2016 |
| CN | 106866253 A | 6/2017 |
| CN | 108147925 A | 6/2018 |
| CN | 108794189 A | 11/2018 |
| IN | 311785 | 1/2012 |
| IN | 326809 | 1/2013 |
| IN | 201941026892 A | 7/2019 |
| IN | 201941029553 A | 8/2019 |
| IN | 391214 | 3/2022 |
| WO | WO2017101691 | 6/2017 |

OTHER PUBLICATIONS

Sayyed et al. 2016 (Recent trends in PGPR Research for Sustainable Crop Productivity; Scientific Publishers, India; IBSN 978-81-7233-990-6; of record). (Year: 2016).*
Kuchimanchi et al. 2019 (IN201941026892A; Kuchimanchi Venkata Satya Sarveswara Sairam and Kuchimanchi Vaishnavi; of record). (Year: 2019).*
IN201941029553A (Kuchimanchi Venkata Satya Sarveswara Sairam and Kuchimanchi Vaishnavi; Aug. 9, 2019) (Year: 2019).*
IN201941026892A (Kuchimanchi Venkata Satya Sarveswara Sairam and Kuchimanchi Vaishnavi; Jul. 12, 2019) (Year: 2019).*
Jaggard KW, et al., "Possible changes to arable crop yields by 2050", . Phil. Trans. R. Soc. B 365:2835-2851 (2010).
Lengke FM, Fleet EM. Southam G (2007) Biosynthesis of silver nanoparticles by filamentous cyanobacteria a from a silver (I) nitrate complex. Langmuir 23:2694-2699 (Abstract).
Mishra, P., et al., "Rejuvenation of Biofertilizer for Sustainable Agriculture and Economic Development", (2014) Consilience: The Journal of Sustainable Development, vol. 11, ISSN. 1, 41-61.
Eichert T, et al., "Size exclusion limits and lateral heterogeneity of the stomatal foliar uptake pathway for aqueous solutes and water-suspended nanoparticles", Physiol Plant 134: 151-160 (2008).
Fu JK, et al., "Spectroscopic characterization on the biosorption and bioreduction of Ag(I) by *Lactobacillus* sp. A09", Acta Phys Chim Sin 16:779-782 (2000).
Notification of Transmittal of the International Search Report and the Written Opinion of the International Searching Authority, or the Declaration for International Application No. PCT/IN2020/050596, "Natural Organic Nano-Fertilizers and Their Process of Production", dated of mailing: Oct. 16, 2020.
Sayyed R.Z et al, "Recent Trends in PGPR Research for Sustainable Crop Productivity" "Scientific Publishers (India)" p. 1-251. (2016).
Prasad R., et al., "Nanotechnology in Sustainable Agriculture: Recent Developments, Challenges and Perspectives", Frontiers in microbiology, 8(1014): 1-13, Jun. 2017.

* cited by examiner

*Primary Examiner* — Mary Maille Lyons
(74) *Attorney, Agent, or Firm* — Hamilton, Brook, Smith & Reynolds, P.C.

(57) ABSTRACT

The present invention deals with the formation of Natural Organic Nano-Fertilizers with the chelated nano-nutrients to balance plant nutrition; improve water holding capacity, soil health improvement, sustainable productivity and quality improvement. The present invention involves production of eco-friendly and low cost process for the synthesis of nanoparticles of nano-nutrients by utilizing microorganisms comprising of two lab adapted strains of *Aspergillus* species, one lab adapted strain of *Lactobacillus* sp. and lactate, gluconate and proteinate salts as a source of nutrient leads to formation of metal nanoparticles (Zn, Mg, Fe and P) with the size of <20 nms. The present invention increases 12-20% of crop yield, stress tolerance of the crops, nutrient mobilization increases and 3 fold increase in nutrient use efficiency.

8 Claims, 6 Drawing Sheets

*TEM image of Zn Nano particles*

*TEM image of Mg Nano particles*

*TEM image of Fe Nano particles*

*TEM image of P Nano particles*

NATURAL ORGANIC NANO-FERTILIZERS AND THEIR PROCESS OF PRODUCTION

This application is the U.S. National Stage of International Application No. PCT/IN2020/050596, filed Jul. 8, 2020, which designates the U.S., published in English, and claims priority under 35 U.S.C. § 119 or 365(c) to Indian Application No. 202041021354, filed May 21, 2020. The entire teachings of the above applications are incorporated herein by reference.

FIELD OF THE INVENTION

The present invention deals with the incorporation of nano-products into agricultural research to have innovative growth of crop yield and giving potentiality for farming. The present invention deals with the formation of Natural Organic Nano-Fertilizers with the chelated nano-nutrients to balance plant nutrition; improve water holding capacity, soil health improvement, sustainable productivity and quality improvement. The present invention includes the synthesis of nanoparticles at lowest possible size leading to effective and enhanced absorption of nutrients into the cells which leads to crop improvement. The present innovation increases 12-20% of crop yield, stress tolerance of the crop, increases nutrient mobilization and 3 fold increase in nutrient use efficiency.

BACKGROUND OF THE INVENTION

In current situation, global uprising in population and rapid urbanization, agronomists and bio fertilizer industrialist are left with the critical duty of feeding more people from agricultural fields which are decreasing correspondingly. The world population is expected to be 9.1 billion people by 2050, to meet the requirement total food consumption will have to rise by 50-70% (Keeney, 1997; Jaggard et al., 2010). Fertilizers have an axial role in enhancing the food production in world especially after the introduction of high yielding crop varieties. Investigations show that, a fertilizer contributes to the tune of 35-40% of the productivity of any crop (Pallabi and Dash, 2014).

Among these, nanotechnology based bio fertilizer's has the potential to revolutionize the agricultural systems and numerous other areas. Nanoparticles are atomic or molecular aggregates with at least one dimension between 1 and 100 nm, which can drastically modify their physicochemical properties compared to the bulk material. Owing to its high surface area to volume size ratio, exhibit significantly novel and improved physical, chemical, and biological properties, phenomena, and functions (Lengke et al, 2007).

The present invention deals with the production and process of natural organic nano-nutrients with Lactate and gluconate technology and its role in sustainability of agriculture. The present study involves biosynthesis of nano-nutrients which are used as nano-fertilizer for sustainable agriculture.

The patent application no: CN 201810822140.5 discloses the preparation of fertilizer using the different raw materials as a source and microorganisms to ferment and produce the bio fertilizer. The preparation steps includes the processing of straw material and treated with the different microorganisms at 25-37° C. for 3-5 days for formation of bio fertilizer.

The patent application no: CN 102017000145701 discloses the bio fertilizer formation through the combination of biological as well as manure components of sheep manure, sweet potato stem, borax, fermented rice chaff and other extracts and components for the soya bean crop. This patent application mainly deals with the increase in the soil absorption capacity of the plant through the roots by the process of microbial based bio fertilizer which was directly involved in the roots and soil of the soya bean. The process of bio fertilizer that acts as a mychorrizal and establish the connection between the plant roots and soil to make the soya bean plant more growth and high chlorophyll content.

The U.S. Pat. No. 311,785 (Application number: 149/DEL/2012) discloses the process of making metal nanoparticles which is through the chemical origin, i.e. using the precursor metal salts. Even though the patent discusses about the nanoparticle formation, but it has higher concentrations of chemical constituents. The nanoparticles are having less bioavailability of nutrients as compared to the organic nano-nutrients. The soil may also be affected when using the inorganic nanoparticles when compared to the organic nano-nutrients.

The patent application number 7/DEL/2013 (U.S. Pat. No. 326,809) discloses the preparation of phosphorous fertilizer by using the nanoparticles. The patent discusses the formation of phosphorous fertilizer using Zn nanoparticles as inducers for phosphorus mobilizing enzymes in rhizosphere. This is an indirect method of preparing the phosphorous fertilizer by using the fungal biomass. This is only biotransformation performed wherein the soil phosphorous was absorbed through the roots by the action of fungal biomass and Zn nanoparticles.

The patent application WO/2017/101691 discloses the preparation of electro neutral metal nanoparticles by using the electro neutral ions. This application mainly deals with the tissue culture of the plants while making the medium incorporate the nanoparticles in ppm levels to the medium. The process described is for the tissue culture plants and is not applicable for all the crops.

The patent application No: CN201610415691.0 discloses the preparation of nano fertilizer synergist from the shrimp shell and extraction of chitin protein from the shrimp waste.

The patent application No: CN201810096140.1 discloses the preparation of bio-organic fertilizer from the following components: corn stalk powder, soybean meal, distillers' grains, rotten chicken manure, fermented coconut shell and camphor bark compost, potassium fulvate, nano-activated diatomite, sodium carboxymethyl cellulose, trace elements and multiple species inoculant. This invention mainly focuses on the soil remediation by using the bio-organic fertilizer.

The patent application No: CN 200710118531.0 (Patent no. CN100534961) discloses the preparation of bio-fertilizer rather than nano-fertilizer. The components of nanometer biological fertilizer and proportions thereof are that: 5-10 percent microbial inoculum, 10-20 percent extract of yeast fermentation liquid, 40-55 percent natural macromolecule organic compound, 15-25 percent urea, 2-4 percent urease inhibitor and 5-15 percent nitrogen, phosphorus and potassium compound fertilizer. The invention accelerates the degradation of macromolecular natural organic compounds into nano-scale organic fertilizers by adding fungicides, and decomposes organic pollutants. At the same time, urea is slowly degraded by adding urease inhibitors, which effectively improves the ability of crops to absorb nutrients and reduce fertilizers.

None of the cited references above disclose or teach what the present invention discloses or teach. The present invention deals with the process of producing organic nano-nutrients by using the Lactate/Gluconate/Proteinate technology with the binding of Zn, Mg, Fe and phosphorous nutrients. The lactates is used as a primary binding source of Zn, Mg and Fe nutrients and proteins are the primary binding source of the phosphorous. The present process of producing the nano-nutrients is very simple, cost effective and produces sustainable form of fertilizer which in turn increases the soil health and yield enhancement of the crops.

SUMMARY OF THE INVENTION

The production of natural organic nano-fertilizers having chelated nano-nutrients has their significant value in the crop yield and increase in the uptake nutrient efficiency. Biological materials when reduced to the Nano scale show some properties which are different from what they exhibit on a macro scale, enabling unique applications. The present invention deals with the application of plant micronutrients as a nano-formulation through the smart delivery systems of lactates and gluconates for soil and foliar applications.

The present invention deals with the formation of Natural Organic Nano-Fertilizers with the chelated nano-nutrients to balance plant nutrition; improve water holding capacity, soil health improvement, sustainable productivity and quality improvement. The present invention includes the synthesis of nanoparticles at lowest possible size leading to effective and enhanced absorption of nutrients into the cells which leads to crop improvement.

In one of the embodiment of the present invention, the process of production of Natural Organic Nano-Fertilizers with the chelated nano-nutrients is carried out in three steps. The step one includes the cultivation of the respective organism for the formation of composites which releases the bioactive components in the solution. The step two includes the formation of Lactate/Gluconate/Proteinate Salt solution and step three is the formation of nano-nutrients with the cultivation of bioactive solution with the lactate/Gluconate (Zn, Mg and Fe)/Proteinate (Phosphorous) salt solution for the formation of nanoparticles.

One of the preferred embodiments of the present invention include that the size of the nanoparticles of the chelated nano-nutrients is below 20 nm which facilitates the diffusion of nutrients along with bioactive components inside the cell and activate the cellular enzymes which lead to increase in the soil nutrient uptake by the plant.

In one of the preferred embodiment of the present invention, the synthesis of nano-nutrients involves growing of the microorganism on selected nutrient source under necessary growth conditions. After the complete growth the biomass is separated. The filtrate is used for isolation of extracellular specific proteins and these are used for nanoparticle synthesis. The selection of microorganism and optimum parameter are specific for synthesis for desired type of nano-nutrients.

Microbial extracellular secreting enzymes are produced which reduce the metal salt of macro or micro scale into nano scale diameter through catalytic effect. Extracellular secretion of enzymes offers the advantage to obtain pure, mono dispersed nanoparticles, which are free from cellular components, associated with downstream processing. Bio sorption and bio reduction were carried out by negative electro kinetic potential of microorganisms enables them to attract the cations and act as trigger of the procedure for biosynthesis of nanoparticles (Fu et al, 2000). These nanoparticles get into plant cells through either stomatal or vascular system which may enhance plant cell metabolic activities that lead to higher crop production. Eichert et al, (2008) suggest that the stomatal pathway is highly capacitive because of its large size exclusion limit and its high transport velocity. Such biologically synthesized, very tiny functional nanoparticles are economically cheap, relatively stable, easy downstream processing and environmentally safe as they are encapsulated by fungal protein which is water soluble.

DETAILED DESCRIPTION OF THE INVENTION

Figure 1:
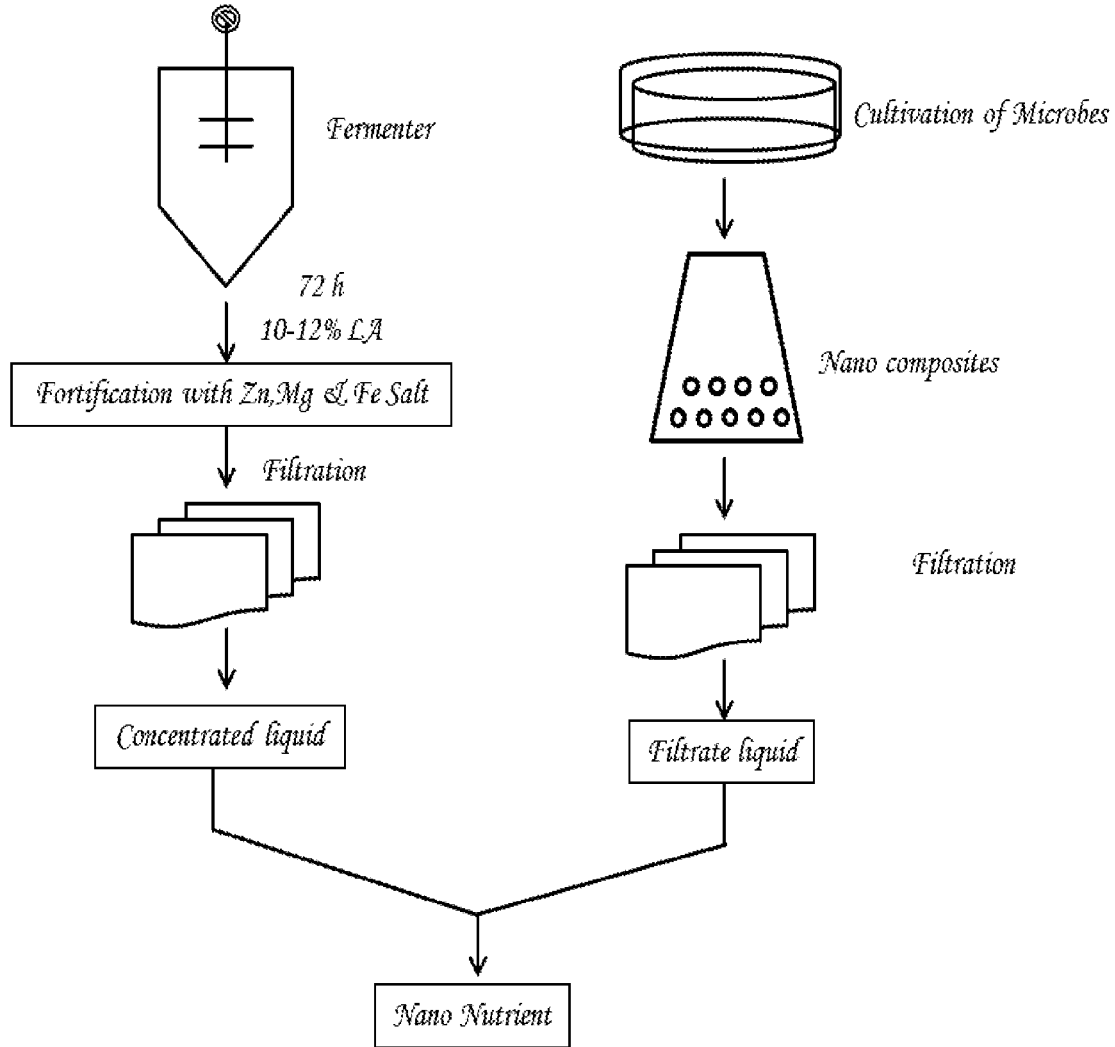
FIG. 1: The process flow diagram for the Nano-nutrient formation through Lactate salts.

The present invention deals with the formation of Natural Organic Nano-Fertilizers with the chelated nano-nutrients to balance plant nutrition; improve water holding capacity, soil health improvement, sustainable productivity and quality improvement. The present invention includes the synthesis of nanoparticles at lowest possible size leading to effective and enhanced absorption of nutrients into the cells which leads to crop improvement.

The present invention deals with the application of plant micronutrients as a nano-formulation through the smart delivery systems of lactates and gluconates for soil and foliar applications.

In one of the embodiment of the present invention, the process of production of Natural Organic Nano-Fertilizers with the chelated nano-nutrients is carried out in three steps:

Step-1: It includes the cultivation of the respective organism for the formation of composites which releases the bioactive components in the solution.

Step-2: It includes the formation of Lactate/Gluconate/Proteinate Salt solution.

Step-3: It includes the cultivation of bioactive solution with the lactate/Gluconate (Zn, Mg and Fe)/Proteinate (Phosphorous) salt solution for the formation of nano-nutrients.

One of the preferred embodiments of the present invention include that the size of the nanoparticles of the chelated nano-nutrients is below 20 nm which facilitates the diffusion of nutrients along with bioactive components inside the cell and activate the cellular enzymes which lead to increase in the soil nutrient uptake by the plant.

In one of the preferred embodiment of the present invention, the synthesis of nano-nutrients involves growing of the microorganism on selected nutrient source under necessary growth conditions. After the complete growth the biomass is separated. The filtrate is used for isolation of extracellular specific proteins and these are used for nanoparticle synthesis. The selection of microorganism and optimum parameter are specific for synthesis for desired type of nano-nutrients.

The present invention is not limited to these examples in any manner. The following examples are intended to illustrate the working of disclosure and not intended to take restrictively to apply any limitations on the scope of the present invention. Those persons skilled in the art will understand that the equivalent substitutes to the specific substances described herein, or the corresponding improvements are considered to be within the scope of the invention.

Experimental Details & Results

The process of production of Natural Organic Nano-Fertilizers with the chelated nano-nutrients is carried out in three steps, Step-1: The formation of Nano composites includes the cultivation of microbial strain in the potato dextrose medium for the formation of Nano composites.

Step-2: The formation of Lactate/Gluconate/Proteinate Salt solution includes the preparation of Zn, Mg and Fe lactate, Zn, Mg and Fe gluconate and Phosphorous proteinate solution.

Step-3: The combination of salt solution (0.5 mM solution) and Nano composite filter (Bioactive solution) leads to formation of Nano-nutrients which includes the cultivation of bioactive solution with the lactate/Gluconate (Zn, Mg and Fe)/Proteinate (Phosphorous) salt solution for 24-48 Hr at 100-120 rpm for the formation of nano-nutrients.

Step-1: The Formation of Nano Composites and Parameters:

In the present invention, the "microbial source" used for nano-nutrient production for zinc, magnesium, ferrous and phosphorous nanoparticle synthesis is *Aspergillus versicolar* (NCIM-698), procured from National Collection for Industrially Important Microorganisms (NCIM), at National Chemical Laboratory, Pune, which is further modified by the way of strain improvement through medium optimization experiments for product yield enhancement at the 'in house R&D section' of Prathista Industries Limited.

The organisms are grown on a potato dextrose agar medium on petri plates containing infusion of potatoes 200 g/L, Dextrose 20 g/L and agar in media 15 g/L. The potato dextrose broth medium was prepared in the conical flasks containing of potatoes 200 g/L and Dextrose 20 g/L and medium was heat sterilized at 121° C. and 15 psi for 25 min in an autoclave. The grown cultures were inoculated into broth medium and incubate at specified conditions.

| | |
|---|---|
| pH: | 6.0 ± 0.5 |
| Temperature: | 30 ± 2° C. |
| Agitation (RPM): | 100-120 |

The temperature was controlled at 30° C., and pH was maintained at 6.0 (unless otherwise specified) using 4N HCl and 4N NaOH or ammonium hydroxide in full strength. Temperature and pH were monitored using temperature and pH probe, respectively (Sartorius). After 84 to 90 hr. incubation, complete formation of composites of biomass has been occurred. The biomass was filtered with Whatmann No-1 filter paper and kept filtrate and biomass in separate. The cell growth was observed by the haziness of the medium and composite formation during the time course of 24-48 hrs.

Step-2: The Formation of Lactate/Gluconate/Proteinate Salt Solutions i. Lactate Salts Preparation and Parameters:

A microbial lab-adapted strain of *Lactobacillus* spp., namely, *Lactobacillus delbrukii* (NCIM 2025) is used for anaerobic fermentation carried out at 45±2° C. on a synthetic medium containing 10-12% glucose, 0.3 g/L yeast extract, 0.3 g/L potassium dihydrogen phosphate, 20 mg/L di-potassium hydrogen phosphate and 10 mg/L magnesium sulphate. Medium (without glucose) was heat sterilized at 121° C. and 15 psi for 25 min in an autoclave. Glucose was sterilized separately at 115° C. for 15 min and added aseptically to rest of the medium. Sterile nitrogen gas was flushed at 0.3 L/min into the headspace of the reactor using a sterile 0.2 μm pore sized PTFE filter (Axiva® 200050 RI, AXIVA Sichem Biotech Pvt. Ltd., India), to maintain anaerobic condition throughout this fermentation step. The pre-sterilized fermentation medium in the bioreactor was inoculated with 10% of inoculum from 48 hrs grown static flask culture. The seed culture is prepared in 500 mL Erlenmeyer flasks, incubated at 45° C. under anaerobic conditions in anaerobic S.S. jars with the help of Whitley Jar Gassing System (Don Whitley Scientific Limited, UK).

| | |
|---|---|
| pH: | 5.5 ± 0.5 |
| Temperature: | 45 ± 2° C. |
| Agitation (RPM): | 100 |
| Nitrogen: | 0.3 L/min |

The temperature is controlled at 45° C., and pH is maintained at 5.5±0.5 using mineral salts. Temperature and pH are monitored using temperature and pH probe, respectively (Sartorius). After 72 hr. fermentation, complete glucose is consumed and salts of Lactic acid concentration of 10-12% are achieved in the fermented broth.

The formation of lactic acid is neutralized with the pre sterilized mineral salts of Zinc magnesium and iron. These are in chelated bioavailable form in the lactate salts. The bio availability of minerals is increased when coupled with organic acid.

Further filtration is performed through Whatmann No-1 filter paper to obtain the nutrient mixture. The filtered product is used for the formation of nanoparticles to get the "Natural Organic Nano-nutrients" with desired nano particle size and efficiency. The upstream process has been depicted in as a flow chart in FIG. 1.

ii. Gluconate Salts Preparation and Parameters:

A microbial lab-adapted strain of *Aspergillus* spp., namely, *Aspergillus niger* (NCIM-704) is used for aerobic fermentation carried out at 28° C.±2° C. on a synthetic medium containing 10-12% glucose, 0.3 g/L yeast extract, 0.5 g/L di-potassium hydrogen phosphate and 10 mg/L magnesium sulphate was heat sterilized at 121° C. and 15 psi for 25 min in an autoclave. Glucose is sterilized separately at 115° C. for 15 min and added aseptically to rest of the medium. Sterile air is flushed at 1-1.5 m3/m3 into the medium from the bottom of the reactor using a sterile 0.2 μm pore sized PTFE filter (Axiva® 200050 RI, AXIVA Sichem Biotech Pvt. Ltd., India), to maintain aerobic condition throughout this fermentation step. The pre-sterilized fermentation medium in the bioreactor was inoculated with 10% of inoculum from 24 hrs grown shaker flask culture. The seed culture is prepared in 500 mL Erlenmeyer flasks, incubated at 28° C. under shaking conditions in temperature controlled orbital shaker.

| pH | 5.5 ± 0.5 |
| Temperature | 28 ± 2° C. |
| Agitation (RPM) | 100 |
| Air Pressure | 1-1.5 m3/m3 |

The temperature is controlled at 28° C., and pH is maintained at 5.5±0.5 using respective mineral salt. Temperature and pH were monitored using temperature and pH probe, respectively (Sartorius). After 24 hr. fermentation, complete glucose is consumed and salts of Gluconic acid concentration of 10-12% is achieved in the fermented broth.

The formation of Gluconic acid was neutralized with the pre sterilized mineral salts of magnesium, zinc and iron. These are in chelated bioavailable form in the gluconate salts. The bio availability of minerals has been increased when coupled with the organic acid salts.

Figure 2:
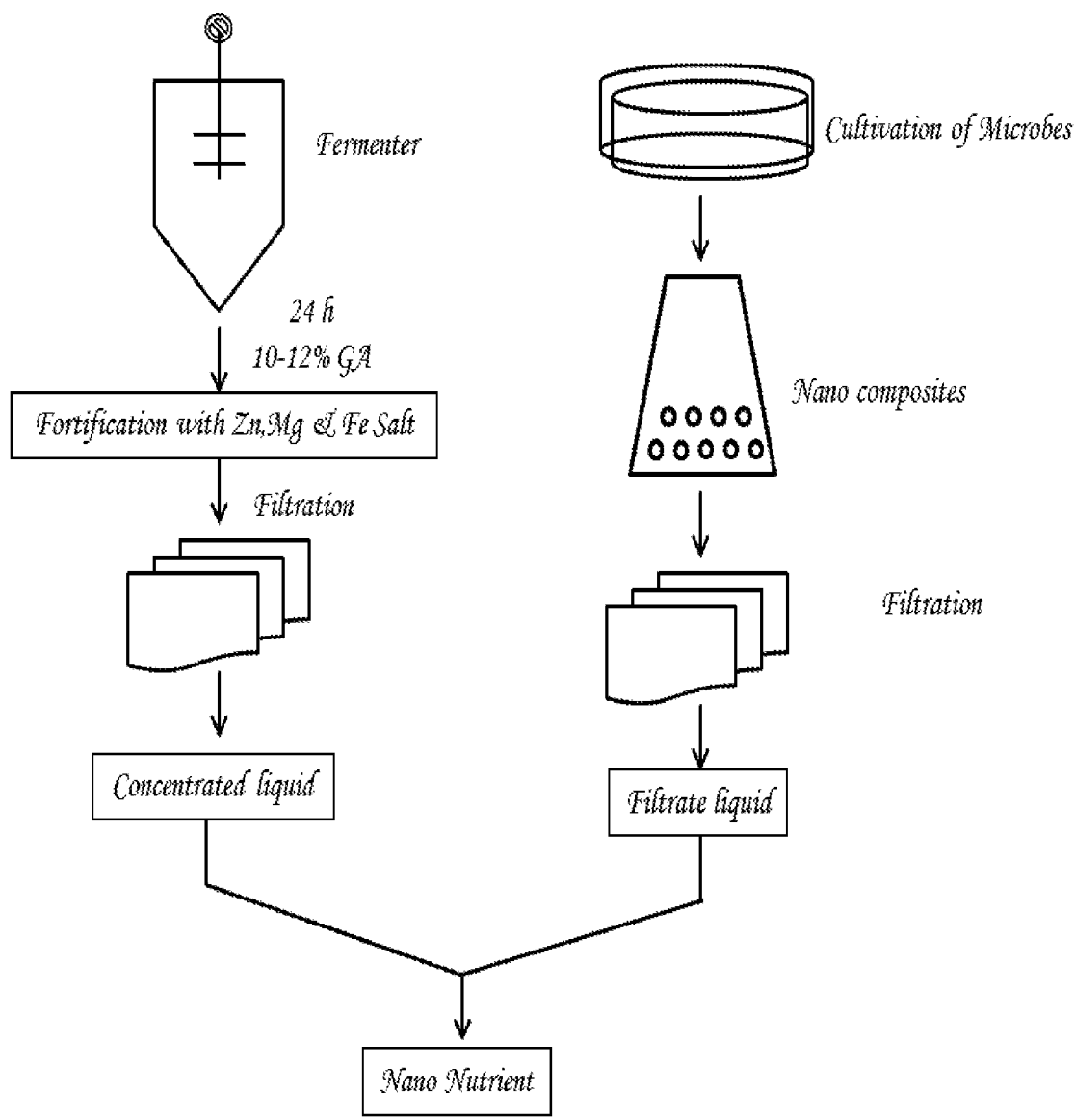
FIG. 2: The process flow diagram for the Nano-nutrient formation through Gluconate salts.
Figure 3:
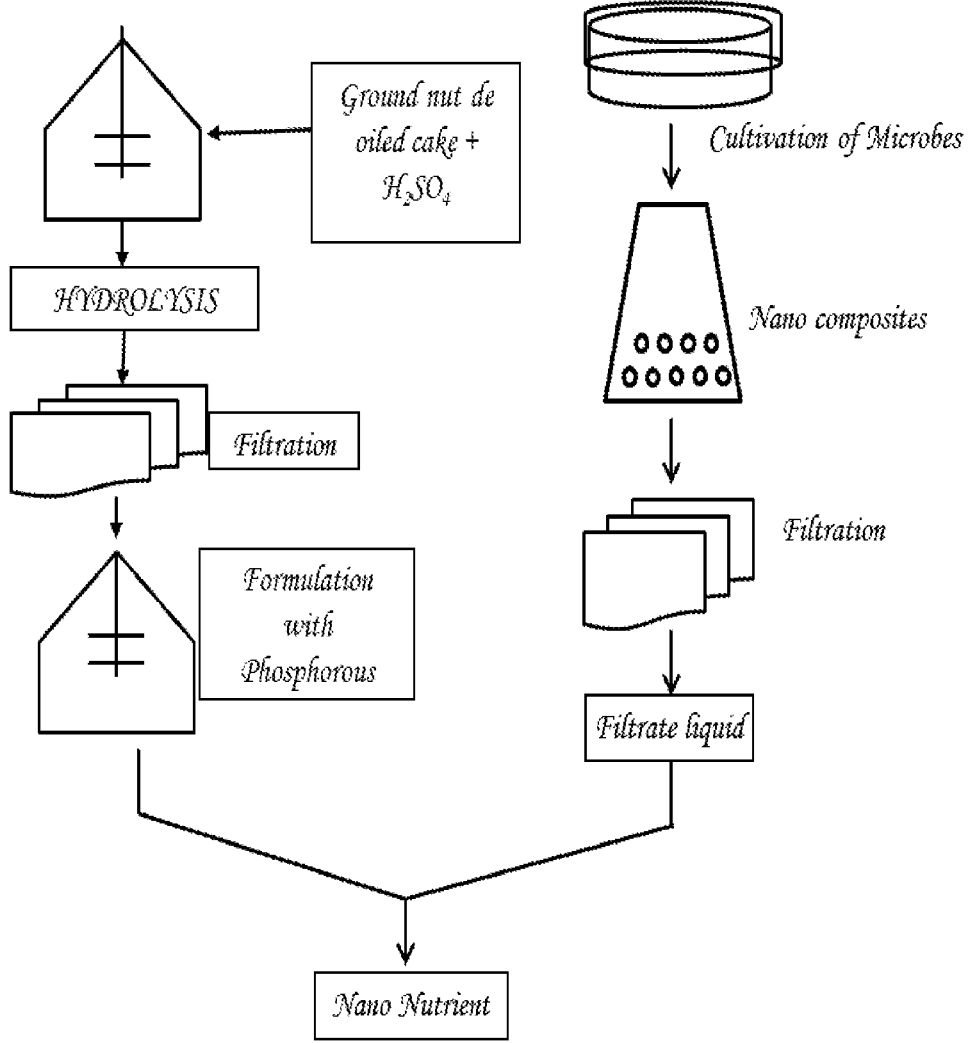
FIG. 3: The process flow diagram for the Nano-nutrient formation through Phosphorous proteinates.

Further filtration is performed through Whatmann No-1 filter paper to obtain the nutrient mixture. The filtered product was used for the formation of Nanoparticles to get the "Natural Organic Nano nutrients" with desired nano particle size and efficiency. The upstream process has been depicted in as a flow chart in FIG. 2.

iii. Phosphorous Proteinates Preparation and Parameters:

The protein hydrolysate is prepared through the groundnut de-oiled cake by using the acid hydrolysis procedure. The groundnut de-oiled cake is dissolved in the water and to it adds 6N sulfuric acid solution and continues stirring for 3-4 hrs at 60-100° C. The formation of protein hydrolysate is having the ammonical nitrogen and this protein hydrolysate liquid was treated with the phosphate salt to form the phosphate protein hydrolysate liquid. This is filtered through the Whatmann no-1 filter paper and filtered product is used for the formation of nanoparticles to get the "Natural Organic Nano-nutrients" with desired nano particle size and efficiency. The process has been depicted in as a flow chart in FIG. 3.

Step-3: Biosynthesis of Natural Organic Nano-Nutrients

The natural organic nutrients is obtained through microbial synthesis of bioactive components and coupled with the nutrient mixture to obtain nano-nutrients. These nutrient mixtures are obtained from the lactate mineral source which is chelated mineral salts.

The filtered biomass was incubated in orbital shaker with the one liter of double distilled water for 24-48 hrs at agitation of 100 rpm to release the bioactive constituents in to the double distilled water. After incubation filter the biomass with Whatmann No-1 filter paper and separate the biomass with the filtrate. The filtrate obtained is having the bioactive constituents like enzymes that have the capability to form the nanoparticles.

The formation of nano-nutrients is the process of incubation with the bioactive constituents with the organic acid salts to obtain the Natural Organic Nano-nutrients. The organic acid salt (Majorly lactate salts) which was having the nutrient which was incubated with the filtrate leads to the formation of nano-nutrient mixture. The reaction of bioactive constituents with the lactate salts upon cleavage of nutrient into the nano-nutrient by the oxidation or reduction process. The formation of nano-nutrient reduces the size of nutrient (metal form) into the nano sized particle which in turn facilitates the diffusion of nutrient into the plant cell along with the bioactive components.

i. Formation of Zn, Mg, Fe and P Natural Organic Nano-Nutrients:

The filtrate obtained from *Aspergillus versicolar* (NCIM-698) is incubated with the Zinc lactate solution of 0.5 mM for 24-48 hrs with the shaking of 100-120 rpm leads to the formation of Zinc Nano nutrient. The solution is filtered through the Whatmann No-1 filter paper and preserve for the analysis and experimentation purpose. The process is performed with the Zinc gluconate solution of 0.5 mM also for 24-48 hrs with the shaking of 100-120 rpm leads to the formation of Zinc Nano nutrient. The solution is filtered through the Whatmann No-1 filter paper and used for the experimentation purpose.

The filtrate obtained from *Aspergillus versicolar* (NCIM-698) is incubated with the Magnesium lactate solution of 0.5 mM for 24-48 hrs with the shaking of 100-120 rpm leads to the formation of Magnesium Nano nutrient. The solution is filtered through the Whatmann No-1 filter paper and preserve for the analysis and experimentation purpose. The process is performed with the Magnesium gluconate solution of 0.5 mM also for 24-48 hrs with the shaking of 100-120 rpm leads to the formation of Magnesium Nano nutrient. The solution is filtered through the Whatmann No-1 filter paper and used for the experimentation purpose.

The filtrate obtained from *Aspergillus versicolar* (NCIM-698) is incubated with the ferrous lactate solution of 0.5 mM for 24-48 hrs with the shaking of 100-120 rpm leads to the formation of Ferrous Nano nutrient. The solution is filtered through the Whatmann No-1 filter paper and preserve for the analysis and experimentation purpose. The process is performed with the ferrous gluconate solution of 0.5 mM also for 24-48 hrs with the shaking of 100-120 rpm leads to the formation of ferrous Nano nutrient. The solution is filtered through the Whatmann No-1 filter paper and used for the experimentation purpose.

The filtrate obtained from *Aspergillus versicolar* (NCIM-698) is incubated with the Phosphorous Proteinate solution of 0.5 mM for 24-48 hrs with the shaking of 100-120 rpm leads to the formation of Phosphorous Nano nutrient. The solution is filtered through the Whatmann No-1 filter paper and preserve for the analysis and experimentation purpose.

ii. Analysis

Figure 4:
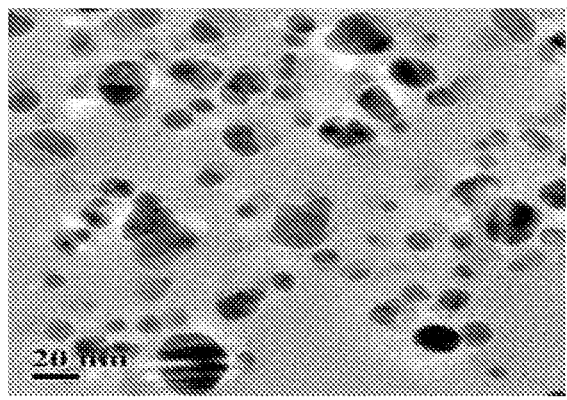
FIG. 4: Transmission electron microscopy images of Zn, Mg and Fe Nanoparticles from the Lactate salts and Phosphorous nanoparticles from proteinates.
Figure 4:
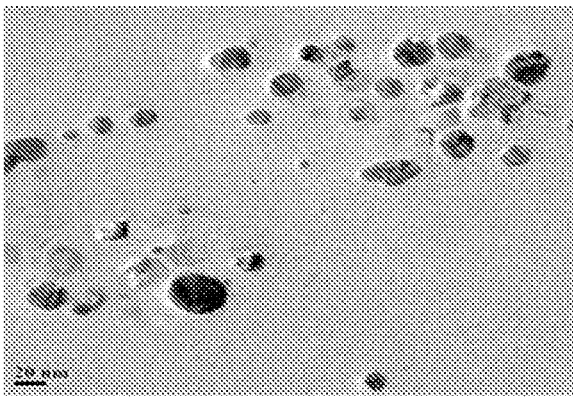
Figure 4:
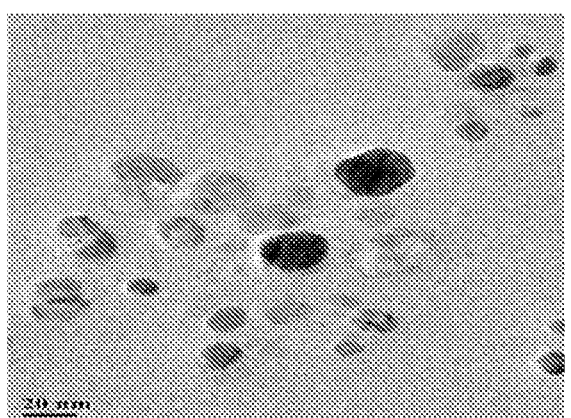
Figure 4:
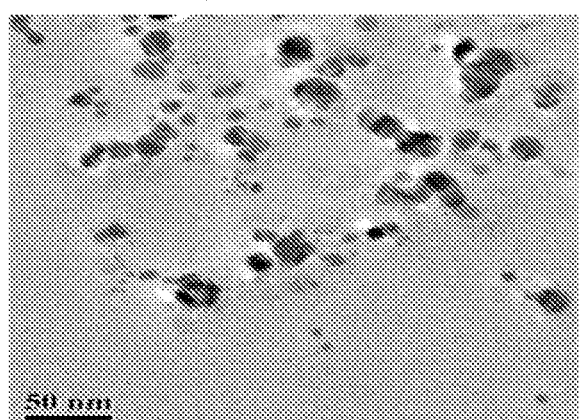

The formation of nanoparticles is measured through the absorbance values and peak shifting of spectroscopy. The exact size shape is determined by the Transmission electron microscopy and energy dispersive spectroscopy for the purity of nano nutrient. The Zn, Mg and Fe nano particles are having the size of the range between 3 nm to 20 nm and phosphorous nano particles are having the size of 5 nm to 20 nm range and spherical in shape (FIG. 4). The nanoparticles which are derived from the lactate source of nutrient have the high efficiency than the gluconate source of nutrient. The phosphorous nanoparticles are having the Proteinate source of amino acids which in turn increase the nutrient content given to the plant along with ammonical nitrogen in addition to the nano-nutrient.

iii. Efficacy Studies

Figure 5:
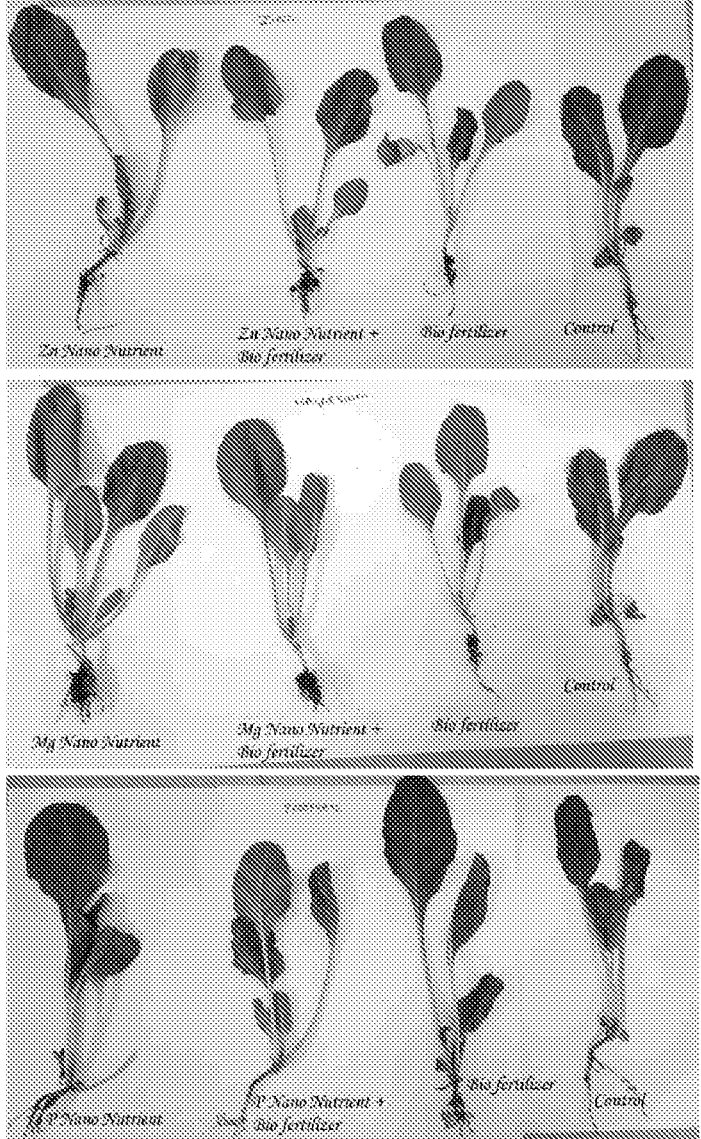
FIG. 5: The efficiency studies of Zn, Mg and P nano-nutrients along with bio-fertilizer and control spinach plants (*Spinacia oleracea* L).

The efficacy studies were performed with the nano-nutrient and bio fertilizer in parallel to facilitate the yield studies. The initial studies were performed on spinach plants (*Spinacia oleracea* L) for the better growth enhancement stated in the FIG. 5. The plants were grown in the controlled environment in the green house and supplied the Nano fertilizers as well as bio fertilizer and also in combinations. The studies were stated that the plants which were treated with the nano nutrient have more chlorophyll content than the remaining plants have shown in Table-1.

TABLE 1

The effect of Nano nutrients and Bio fertilizers
on Spinach plant (*Spinacia oleracea L*)

| S. No | Contents | Chlorophyll a | Chlorophyll b | Total chlorophyll content (% age increase in comparison to the control) |
|---|---|---|---|---|
| 01. | Control | 14.29 | 4.89 | 19.18 |
| 02. | Nano-Zn | 19.49 | 7.24 | 26.74 (39.40%) |
| 03. | Nano-P | 19.79 | 7.33 | 27.12 (41.40%) |
| 04. | Nano-Mg | 24.79 | 9.42 | 34.21 (78.38%) |
| 05. | Bio-Zn | 15.87 | 5.62 | 21.49 (12.00%) |
| 06. | Bio-P | 15.84 | 6.12 | 21.96 (14.50%) |
| 07. | Bio-Mg | 16.64 | 6.08 | 22.72 (18.45%) |
| 08. | Nano-Zn + Bio-Zn | 20.54 | 7.92 | 28.46 (48.38%) |
| 09. | Nano-P + Bio-P | 21.74 | 8.09 | 29.83 (55.50%) |
| 10. | Nano-Mg + Bio-Mg | 25.53 | 9.18 | 34.72 (81.00%) |

Crop yields and Soil index can be improved with the adoption of innovative technologies in farmer fields like biosynthesized nano nutrients and Organic acid based bio-tech formulations through integrated nutrient management. The recommended doses are 10 ppm for Zn, 20 ppm for Mg, 30 ppm for Fe and 40 ppm for P.

The crop yield studies were performed in the rabhi season in separate blocks for the wheat crop. The wheat crop was treated with the following materials to analyze the efficacy of the nano nutrients.

1. Control Plants: This is the untreated group of plants.

2. Bio-Mg Treated plants: This is the group treated with the Organic bio fertilizer bio magnesium composed of magnesium lactate and magnesium gluconate combination.

3. Bio-P Treated plants: this is the group treated with the organic Bio Phos composed of amino acid based phosphorous.

4. Bio-Zn Treated Plants: This is the group treated with the organic biofertilizer bio zinc composed of Zinc lactate and zinc gluconate combination.

5. Nano Fe Treated plants: This is the group treated with the Fe Organic Nano Nutrient.

6. Nano Mg Treated plants: This is the group treated with the Mg Organic Nano Nutrient.

7. Nano P Treated plants: This is the group treated with the P Organic Nano Nutrient.

8. Nano Zn Treated plants: This is the group treated with the Zn Organic Nano Nutrient.

The wheat crop is treated with the control group which is untreated of any fertilizer and three variants of bio fertilizers which was having the composition of organic lactate and gluconate based whereas phosphorous organic fertilizer which is amino acid based formulation. The $2^{nd}$ set of treated group was organic Nano nutrients of four metal groups. The experimental outcome in table 2 clearly shows the usage of nano-fertilizers leads to increased grain yield productivity to 12-18% when compared to the control group. It clearly demonstrates that the nano nutrient usage results in more yield than the organic fertilizers. The studies clearly indicates that the crop which is treated with nano-nutrient there is threefold increase in the yield.

TABLE 2

Effect of Nano nutrients and bio fertilizers on wheat crop

| S. No | Treatment | Grain yield(Kg/ha) Wheat |
|---|---|---|
| 01. | Control | 3856 |
| 02. | Bio-Mg | 4025 (4.4%) |
| 03. | Bio-P | 4118 (6.8%) |
| 04. | Bio-Zn | 4221 (9.5%) |
| 05. | Nano-Fe | 4318 (12.0%) |
| 06. | Nano-Mg | 4489 (16.4%) |
| 07. | Nano-P | 4582 (18.8%) |
| 08. | Nano-Zn | 4502 (16.8%) |

Figure 6:
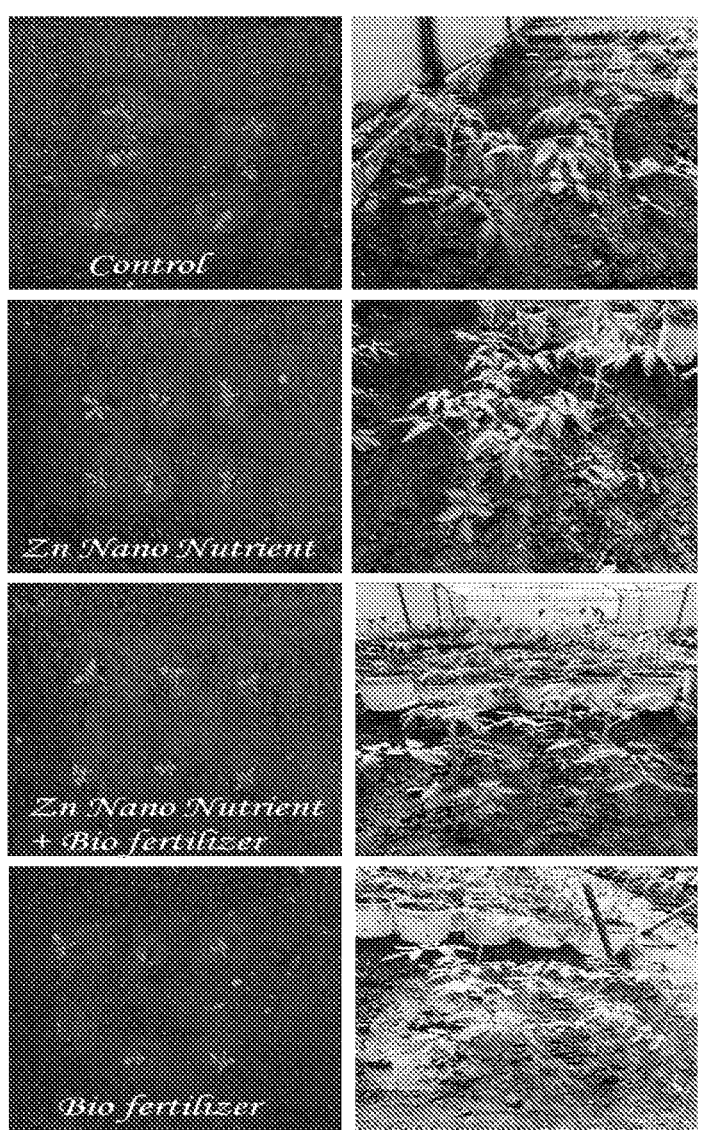
FIG. 6: The efficiency studies of Zn nano-nutrient along with bio-fertilizer and control Tomato plants (*Solanum lycopersicum* L.).

The shoot length studies were performed for the Tomato plant (*Solanum lycopersicum* L.) which is depicted in the FIG. 6. The plant studies were performed in a controlled environment in the green house. The Zn nano nutrient along with Zn bio fertilizer used for the study. The efficiency of Zn nano nutrient stated that it has much varied shoot length and the shoot length further increased when it has used along with bio fertilizer (Table-3).

TABLE 3

The nano efficacy studies have been conducted on Tomato plant (*Solatium lycopersicum L.*) for the Zn nano fertilizer along with the Bio Zn fertilizer.

| S. No | Contents | Avg. Shoot Length (cm) |
|---|---|---|
| 01. | Control | 25.50* |
| 02. | Nano Zn | 35.33* |
| 03. | Bio Zn | 30.00* |
| 04. | Nano + Bio Zn | 37.16* |

*The values shown in the table are the average of the triplicate in cms.

The nano-nutrient used for the efficiency study is the lactate based nano-nutrient and proteinate based phosphorous nutrient. The nano-nutrient usage is compatible with the bio-fertilizers and has nontoxic effect to the plants as well as humans which in turn produces the higher yields than the fertilizers. The nano fertilizers comprises of the combination of nano particles, nutrients and bio active constituents along with the bio available form of lactates, gluconates and proteinates form.

The Nano-nutrients bounded lacto-gluconate based products, not only ensures the supply of particular nutrient to the soil and crop, but they also enhances microbial activity by supplying carbon rich organic acids particularly glucose, an ideal food source for soil microorganisms and increases biological activity and soil organic carbon (SOC). The protein hydrolysate based products from vegetable protein and sea weed are rich source of soluble proteins and amino acids; hence act as growth promoters and ideal microbial activity enhancers and grain yield.

INDUSTRIAL APPLICABILITY OF THE INVENTION

The natural organic Nano-nutrients are the active nutrients into agriculture to cope up the crop yield and enhance the bioavailability of nutrients for the plants. The Nano-nutrients play a vital role in the agricultural industry to decrease the usage of chemical based fertilizers and balance the plant nutrition and soil health. In addition, it enhances the stress tolerance by the crop, nutrient mobilization and 3 fold increase in nutrient use efficiency.

REFERENCES

1. Jaggard K W, Qi A, Ober E S. (2010) Possible changes to arable crop yields by 2050. Phil. Trans. R. Soc. B 365: 2835-2851
2. Keeney D (1997) What goes around comes around—The nitrogen issues cycle. In: Mortwedt J J, Shaviv A (eds), proceeding of 3th International Dahlia Greidinger Symposium on Fertilization and The Environment, Haifa.
3. Lengke F M, Fleet E M, Southam G (2007) Biosynthesis of silver nanoparticles by filamentous cyanobacteria a from a silver (I) nitrate complex. Langmuir 23:2694-2699
4. Pallabi Mishra, Debiprasad Dash (2014) Rejuvenation of Biofertilizer for Sustainable Agriculture and Economic Development, Consilience: The Journal of Sustainable Development, Vol. 11, ISSN. 1, 41-61
5. Eichert T, Kurtz A, Steiner U, Goldbach H E (2008) Size exclusion limits and lateral heterogeneity of the stomatal foliar uptake pathway for aqueous solutes and water-suspended nanoparticles. Physiol Plant 134:151-160
6. Fu J K, Liu Y Y, Gu P Y, Tang D L, Lin Z Y, Yao B X, Wen S Z (2000) Spectroscopic characterization on the biosorption and bioreduction of Ag(I) by *Lactobacillus* sp. A09. Acta Phys Chim Sin 16:779-782.
7. Mei Wei (2018) Chinese patent application no. 201810822140.5 dt. 13 Nov. 2018 retrieved from https://patents.google.com/patent/CN108794189A.
8. Fan Chengzhen, Zhang Weiguo, Zhang Zongxi (2017) Chinese patent application no. 102017000145701 dt. 13 Mar. 2017 retrieved from https://patents.google.com/patent/CN106866253A.
9. Tarafdar J C, Ramesh Raliya (2012) Indian patent publication number 149/DEL/2012. dt.18 Jan. 2012.
10. Tarafdar J C, Ramesh Raliya (2013) Indian patent publication number 7/DEL/2013. dt.2 Jan. 2013.
11. Hui Zhao, Min Liu, Yu Chen, et al., (2016) patent application no. PCT/CN2016/108424 dt. Feb. 12, 2016 retrieved from https://patents.google.com/patent/WO2017101691A1.
12. Ying Donghui, Shi Rongguang, Zheng Xiangqun, Ding Yongzhen, Wang Pengju (2016) Chinese patent application no. 201610415691.0 dt. 13 Jan. 2016 retrieved from https://patents.google.com/patent/CN106242712A.
13. Wu Haisheng (2018) Chinese patent application no. 201810096140.1 dt. 31 Jul. 2018 retrieved from https://patents.google.com/patent/CN108147925A.
14. Yan Wang, Jiu Jiukang, Shen Yuzhi (2007) Chinese patent application no. 200710118531.0 dt. 9 Jul. 2007 retrieved from https://patents.google.com/patent/CN101113120A.

We claim:

1. A process for producing an organic nano-fertilizer with chelated nano-nutrients, comprising:

(i) producing biomass from fermentation of *Aspergillus versicolor* NCIM-698 in potato dextrose medium, filtering the biomass and collecting filtrate as a bioactive solution which comprises nano composites from the biomass;

(ii) forming lactate and gluconate salt solutions, wherein *Lactobacillus delbrueckii* NCIM 2025 is used under anaerobic fermentation conditions to produce lactic acid fermentation product and then fortifying the lactic acid with zinc, magnesium and iron to produce zinc lactate, magnesium lactate and ferrous lactate salt solutions; and wherein *Aspergillus niger* NCIM-704 is used under aerobic fermentation conditions to produce gluconic acid fermentation product and then fortifying the gluconic acid with zinc, magnesium and iron to produce zinc gluconate, magnesium gluconate and ferrous gluconate salt solutions; and (iii) incubating the salt solution of (ii), a phosphorus proteinate hydrolysate solution, and the filtrate of (i) together for 24-48 hours at 100-120 rpm to produce the organic nano-fertilizer with chelated nano-nutrients having a nanoparticle size of 20 nm or less.

2. The process as claimed in claim 1, wherein lactate salts are prepared using *Lactobacillus delbrueckii* NCIM 2025 by anaerobic fermentation carried out at $45 \pm 2°$ C. on a synthetic medium containing 10-12% glucose, 0.3 g/L yeast extract, 0.3 g/L potassium dihydrogen phosphate, 20 mg/L di-potassium hydrogen phosphate and 10 mg/L magnesium sulphate.

3. The process as claimed in claim 1, wherein gluconate salts are prepared using *Aspergillus niger* NCIM-704 by aerobic fermentation carried out at $28°$ C.$\pm 2°$ C. on a synthetic medium containing 10-12% glucose, 0.3 g/L yeast extract, 0.5 g/L di-potassium hydrogen phosphate and 10 mg/L magnesium sulphate.

4. The process as claimed in claim 1, wherein the protein hydrolysate is prepared from a groundnut de-oiled cake by acid hydrolysis.

5. An organic nano-fertilizer with chelated nano-nutrients, comprising nanoparticles of chelated nano-nutrients comprising zinc lactate salts, magnesium lactate salts, ferrous lactate salts, zinc gluconate salts, magnesium gluconate salts and ferrous gluconate salts, and a phosphorus proteinate hydrolysate, and wherein the nanoparticles of the chelated nano-nutrients are 20 nm or less.

6. The organic nano-fertilizer as claimed in claim 5, wherein the nanoparticles are Zn, Mg and Fe nanoparticles having a particle size between 3 nm to 20 nm, and wherein the nanoparticles are spherical in shape.

7. The organic nano-fertilizer as claimed in claim 5, wherein the nanoparticles are phosphorus nanoparticles having a particle size of 5 nm to 20 nm, and wherein the nanoparticles are spherical in shape.

8. The process as claimed in claim 1, wherein each of the phosphorus proteinate solution, zinc lactate, zinc gluconate, magnesium lactate, magnesium gluconate, ferrous lactate and ferrous gluconate are added to (iii) at a concentration of 0.5 mM.

* * * * *